(12) United States Patent
Miyake et al.

(10) Patent No.: US 7,094,948 B2
(45) Date of Patent: Aug. 22, 2006

(54) TRANSGENIC ANIMALS

(75) Inventors: Akira Miyake, Tsukuba (JP); Yukihiro Nakamura, Tsukuba (JP); Jianwei Ni, Tsukuba (JP); Shinobu Mochizuki, Tsukuba (JP)

(73) Assignee: Astellas Pharma, Inc., Tokyo (JP)

( * ) Notice: Subject to any disclaimer, the term of this patent is extended or adjusted under 35 U.S.C. 154(b) by 110 days.

(21) Appl. No.: 10/493,943

(22) PCT Filed: Nov. 13, 2002

(86) PCT No.: PCT/JP02/11843

§ 371 (c)(1),
(2), (4) Date: Apr. 28, 2004

(87) PCT Pub. No.: WO03/041496

PCT Pub. Date: May 22, 2003

(65) Prior Publication Data

US 2004/0210952 A1    Oct. 21, 2004

(30) Foreign Application Priority Data

Nov. 14, 2001  (JP)  ............... 2001-349288

(51) Int. Cl.
A01K 67/027  (2006.01)
(52) U.S. Cl. ........................... 800/18; 800/3
(58) Field of Classification Search .......... 800/8, 800/18
See application file for complete search history.

(56) References Cited

U.S. PATENT DOCUMENTS

| 6,326,168 B1 | 12/2001 | Miyake et al. |
| 6,518,398 B1 | 2/2003 | Curtis |
| 2003/0104429 A1 | 6/2003 | Curtis |

FOREIGN PATENT DOCUMENTS

| WO | WO 99/43696 A1 | 9/1999 |
| WO | WO 00/01819 A1 | 1/2000 |
| WO | WO 00/05346 A1 | 2/2000 |
| WO | WO 00/09534 | * | 2/2000 |
| WO | WO 00/09534 A1 | 2/2000 |
| WO | WO 00/22001 A2 | 4/2000 |
| WO | WO 03/016475 A2 | 2/2003 |

OTHER PUBLICATIONS

Picciotto MR, Using knockout and transgenic mice to study neurophysiology and behavior, 1998, Physiological Reviews, vol. 78, pp. 1131-1163.*
Miyake A, New ether-a-go-go K channel family members localized in human telencephalon, 1999, JBC, vol. 274, pp. 25018-25025.*
Montoliu L, Gene transfer strategies in animal transgenesis, 2002, Cloning and Stem Cells, vol. 4, pp. 39-46.*
Smith KR, Gene transfer in higher animals: theoretical considerations and key concepts, J. of Biotechnology, vol. 99, pp. 1-22.*
Ristevski S, Making better transgenic models, 2005, Molecular Biotechnology, vol. 29, pp. 153-163.*
Houdebine LM, The methods to generate transgenic animals and to control transgene expression, 2002, J. of Biotechnology, vol. 98, pp. 145-160.*
Mark Mayford et al., "The 3'-untranslated region of CaMKH$\alpha$ is a cis-acting singal for the localization and translation of mRNA in dendrites", Proc. Natl. Acad. Sci. (1996) USA, vol. 93, pp. 13250-13255.
Akira Miyake et al., "New Ether-$\alpha$-go-go K$^+$ Channel Family Members Localized in Human Telencephalon*", The Journal of Biological Chemistry 91999), vol. 274, No. 35, pp. 25018-25025.

* cited by examiner

Primary Examiner—Ram R. Shukla
Assistant Examiner—David A. Montanari
(74) Attorney, Agent, or Firm—Sughrue Mion, PLLC (57) ABSTRACT

There is discloses a transgenic mouse over-expressing a potassium channel BEC1, which can be used as an effective tool for screening a substance for antidementia or a substance to improve learning and memory.

Also disclosed are an in vivo screening method of a substance for antidementia or a substance to improve learning and memory, which uses the learning and memory abilities of said mouse as the index, and an in vivo screening of a substance for antianxiety, which uses acceleration of anxiety as the index.

In addition, there is disclosed a method for producing a pharmaceutical composition for antidementia, learning and memory improvement use or antianxiety, using a substance capable of inhibiting the learning and memory potassium channel activity as the active ingredient which can be obtained by the aforementioned screening method of the present invention.

5 Claims, 2 Drawing Sheets

FIG. 1

*FIG. 2*

SEQUENCE LISTING

<160> NUMBER OF SEQ ID NOS: 12

<210> SEQ ID NO 1
<211> LENGTH: 3252
<212> TYPE: DNA
<213> ORGANISM: Homo sapiens
<220> FEATURE:
<221> NAME/KEY: CDS
<222> LOCATION: (1)..(3252)

<400> SEQUENCE: 1

```
atg ccg gcc atg cgg ggc ctc ctg gcg cct cag aac acc ttc ctg gac        48
Met Pro Ala Met Arg Gly Leu Leu Ala Pro Gln Asn Thr Phe Leu Asp
1               5                   10                  15 acc atc gct acg cgc ttc gac ggc acg cac agt aac ttc gtg ctg ggc        96
Thr Ile Ala Thr Arg Phe Asp Gly Thr His Ser Asn Phe Val Leu Gly
                20                  25                  30 aac gcc cag gtg gcg ggg ctc ttc ccc gtg gtc tac tgc tct gat ggc       144
Asn Ala Gln Val Ala Gly Leu Phe Pro Val Val Tyr Cys Ser Asp Gly
            35                  40                  45 ttc tgt gac ctc acg ggc ttc tcc cgg gct gag gtc atg cag cgg ggc       192
Phe Cys Asp Leu Thr Gly Phe Ser Arg Ala Glu Val Met Gln Arg Gly
        50                  55                  60 tgt gcc tgc tcc ttc ctt tat ggg cca gac acc agt gag ctc gtc cgc       240
Cys Ala Cys Ser Phe Leu Tyr Gly Pro Asp Thr Ser Glu Leu Val Arg
65                  70                  75                  80 caa cag atc cgc aag gcc ctg gac gag cac aag gag ttc aag gct gag       288
Gln Gln Ile Arg Lys Ala Leu Asp Glu His Lys Glu Phe Lys Ala Glu
                85                  90                  95 ctg atc ctg tac cgg aag agc ggg ctc ccg ttc tgg tgt ctc ctg gat       336
Leu Ile Leu Tyr Arg Lys Ser Gly Leu Pro Phe Trp Cys Leu Leu Asp
                100                 105                 110 gtg ata ccc ata aag aat gag aaa ggg gag gtg gct ctc ttc cta gtc       384
Val Ile Pro Ile Lys Asn Glu Lys Gly Glu Val Ala Leu Phe Leu Val
            115                 120                 125 tct cac aag gac atc agc gaa acc aag aac cga ggg ggc ccc gac aga       432
Ser His Lys Asp Ile Ser Glu Thr Lys Asn Arg Gly Gly Pro Asp Arg
        130                 135                 140 tgg aag gag aca ggt ggt ggc cgg cgc cga tat ggc cgg gca cga tcc       480
Trp Lys Glu Thr Gly Gly Gly Arg Arg Arg Tyr Gly Arg Ala Arg Ser
145                 150                 155                 160 aaa ggc ttc aat gcc aac cgg cgg cgg agc cgg gcc gtg ctc tac cac       528
Lys Gly Phe Asn Ala Asn Arg Arg Arg Ser Arg Ala Val Leu Tyr His
                165                 170                 175 ctg tcc ggg cac ctg cag aag cag ccc aag ggc aag cac aag ctc aat       576
Leu Ser Gly His Leu Gln Lys Gln Pro Lys Gly Lys His Lys Leu Asn
            180                 185                 190 aag ggg gtg ttt ggg gag aaa cca aac ttg cct gag tac aaa gta gcc       624
Lys Gly Val Phe Gly Glu Lys Pro Asn Leu Pro Glu Tyr Lys Val Ala
        195                 200                 205 gcc atc cgg aag tcg ccc ttc atc ctg ttg cac tgt ggg gca ctg aga       672
Ala Ile Arg Lys Ser Pro Phe Ile Leu Leu His Cys Gly Ala Leu Arg
    210                 215                 220 gcc acc tgg gat ggc ttc atc ctg ctc gcc aca ctc tat gtg gct gtc       720
Ala Thr Trp Asp Gly Phe Ile Leu Leu Ala Thr Leu Tyr Val Ala Val
225                 230                 235                 240 act gtg ccc tac agc gtg tgt gtg agc aca gca cgg gag ccc agt gcc       768
Thr Val Pro Tyr Ser Val Cys Val Ser Thr Ala Arg Glu Pro Ser Ala
                245                 250                 255
```

-continued

| | | |
|---|---|---|
| gcc cgc ggc ccg ccc agc gtc tgt gac ctg gcc gtg gag gtc ctc ttc<br>Ala Arg Gly Pro Pro Ser Val Cys Asp Leu Ala Val Glu Val Leu Phe<br>260                            265                    270 | 816 |
| atc ctt gac att gtg ctg aat ttc cgt acc aca ttc gtg tcc aag tcg<br>Ile Leu Asp Ile Val Leu Asn Phe Arg Thr Thr Phe Val Ser Lys Ser<br>275                            280                    285 | 864 |
| ggc cag gtg gtg ttt gcc cca aag tcc att tgc ctc cac tac gtc acc<br>Gly Gln Val Val Phe Ala Pro Lys Ser Ile Cys Leu His Tyr Val Thr<br>290                            295                    300 | 912 |
| acc tgg ttc ctg ctg gat gtc atc gca gcg ctg ccc ttt gac ctg cta<br>Thr Trp Phe Leu Leu Asp Val Ile Ala Ala Leu Pro Phe Asp Leu Leu<br>305                            310                    315                  320 | 960 |
| cat gcc ttc aag gtc aac gtg tac ttc ggg gcc cat ctg ctg aag acg<br>His Ala Phe Lys Val Asn Val Tyr Phe Gly Ala His Leu Leu Lys Thr<br>                      325                    330                    335 | 1008 |
| gtg cgc ctg ctg cgc ctg ctg cgc ctg ctt ccg cgg ctg gac cgg tac<br>Val Arg Leu Leu Arg Leu Leu Arg Leu Leu Pro Arg Leu Asp Arg Tyr<br>                      340                    345                    350 | 1056 |
| tcg cag tac agc gcc gtg gtg ctg aca ctg ctc atg gcc gtg ttc gcc<br>Ser Gln Tyr Ser Ala Val Val Leu Thr Leu Leu Met Ala Val Phe Ala<br>                      355                    360                    365 | 1104 |
| ctg ctc gcg cac tgg gtc gcc tgc gtc tgg ttt tac att ggc cag cgg<br>Leu Leu Ala His Trp Val Ala Cys Val Trp Phe Tyr Ile Gly Gln Arg<br>370                            375                    380 | 1152 |
| gag atc gag agc agc gaa tcc gag ctg cct gag att ggc tgg ctg cag<br>Glu Ile Glu Ser Ser Glu Ser Glu Leu Pro Glu Ile Gly Trp Leu Gln<br>385                            390                    395                  400 | 1200 |
| gag ctg gcc cgc cga ctg gag act ccc tac tac ctg gtg ggc cgg agg<br>Glu Leu Ala Arg Arg Leu Glu Thr Pro Tyr Tyr Leu Val Gly Arg Arg<br>                      405                    410                    415 | 1248 |
| cca gct gga ggg aac agc tcc ggc cag agt gac aac tgc agc agc agc<br>Pro Ala Gly Gly Asn Ser Ser Gly Gln Ser Asp Asn Cys Ser Ser Ser<br>                      420                    425                    430 | 1296 |
| agc gag gcc aac ggg acg ggg ctg gag ctg ctg ggc ggc ccg tcg ctg<br>Ser Glu Ala Asn Gly Thr Gly Leu Glu Leu Leu Gly Gly Pro Ser Leu<br>                      435                    440                    445 | 1344 |
| cgc agc gcc tac atc acc tcc ctc tac ttc gca ctc agc agc ctc acc<br>Arg Ser Ala Tyr Ile Thr Ser Leu Tyr Phe Ala Leu Ser Ser Leu Thr<br>450                            455                    460 | 1392 |
| agc gtg ggc ttc ggc aac gtg tcc gcc aac acg gac acc gag aag atc<br>Ser Val Gly Phe Gly Asn Val Ser Ala Asn Thr Asp Thr Glu Lys Ile<br>465                            470                    475                  480 | 1440 |
| ttc tcc atc tgc acc atg ctc atc ggc gcc ctg atg cac gcg gtg gtg<br>Phe Ser Ile Cys Thr Met Leu Ile Gly Ala Leu Met His Ala Val Val<br>                      485                    490                    495 | 1488 |
| ttt ggg aac gtg acg gcc atc atc cag cgc atg tac gcc cgc cgc ttt<br>Phe Gly Asn Val Thr Ala Ile Ile Gln Arg Met Tyr Ala Arg Arg Phe<br>                      500                    505                    510 | 1536 |
| ctg tac cac agc cgc acg cgc gac ctg cgc gac tac atc cgc atc cac<br>Leu Tyr His Ser Arg Thr Arg Asp Leu Arg Asp Tyr Ile Arg Ile His<br>                      515                    520                    525 | 1584 |
| cgt atc ccc aag ccc ctc aag cag cgc atg ctg gag tac ttc cag gcc<br>Arg Ile Pro Lys Pro Leu Lys Gln Arg Met Leu Glu Tyr Phe Gln Ala<br>530                            535                    540 | 1632 |
| acc tgg gcg gtg aac aat ggc atc gac acc acc gag ctg ctg cag agc<br>Thr Trp Ala Val Asn Asn Gly Ile Asp Thr Thr Glu Leu Leu Gln Ser<br>545                            550                    555                  560 | 1680 |
| ctc cct gac gag ctg cgc gca gac atc gcc atg cac ctg cac aag gag<br>Leu Pro Asp Glu Leu Arg Ala Asp Ile Ala Met His Leu His Lys Glu<br>                      565                    570                    575 | 1728 |

|  |  |
|---|---|
| gtc ctg cag ctg cca ctg ttt gag gcg gcc agc cgc ggc tgc ctg cgg<br>Val Leu Gln Leu Pro Leu Phe Glu Ala Ala Ser Arg Gly Cys Leu Arg<br>580                     585                     590 | 1776 |
| gca ctg tct ctg gcc ctg cgg ccc gcc ttc tgc acg ccg ggc gag tac<br>Ala Leu Ser Leu Ala Leu Arg Pro Ala Phe Cys Thr Pro Gly Glu Tyr<br>      595                     600                     605 | 1824 |
| ctc atc cac caa ggc gat gcc ctg cag gcc ctc tac ttt gtc tgc tct<br>Leu Ile His Gln Gly Asp Ala Leu Gln Ala Leu Tyr Phe Val Cys Ser<br>610                     615                     620 | 1872 |
| ggc tcc atg gag gtg ctc aag ggt ggc acc gtg ctc gcc atc cta ggg<br>Gly Ser Met Glu Val Leu Lys Gly Gly Thr Val Leu Ala Ile Leu Gly<br>625                     630                     635                     640 | 1920 |
| aag ggc gac ctg atc ggc tgt gag ctg ccc cgg cgg gag cag gtg gta<br>Lys Gly Asp Leu Ile Gly Cys Glu Leu Pro Arg Arg Glu Gln Val Val<br>                    645                     650                     655 | 1968 |
| aag gcc aat gcc gac gtg aag ggg ctg acg tac tgc gtc ctg cag tgt<br>Lys Ala Asn Ala Asp Val Lys Gly Leu Thr Tyr Cys Val Leu Gln Cys<br>660                     665                     670 | 2016 |
| ctg cag ctg gct ggc ctg cac gac agc ctt gcg ctg tac ccc gag ttt<br>Leu Gln Leu Ala Gly Leu His Asp Ser Leu Ala Leu Tyr Pro Glu Phe<br>      675                     680                     685 | 2064 |
| gcc ccg cgc ttc agt cgt ggc ctc cga ggg gag ctc agc tac aac ctg<br>Ala Pro Arg Phe Ser Arg Gly Leu Arg Gly Glu Leu Ser Tyr Asn Leu<br>690                     695                     700 | 2112 |
| ggt gct ggg gga ggc tct gca gag gtg gac acc agc tcc ctg agc ggc<br>Gly Ala Gly Gly Gly Ser Ala Glu Val Asp Thr Ser Ser Leu Ser Gly<br>705                     710                     715                     720 | 2160 |
| gac aat acc ctt atg tcc acg ctg gag gag aag gag aca gat ggg gag<br>Asp Asn Thr Leu Met Ser Thr Leu Glu Glu Lys Glu Thr Asp Gly Glu<br>                    725                     730                     735 | 2208 |
| cag ggc ccc acg gtc tcc cca gcc cca gct gat gag ccc tcc agc ccc<br>Gln Gly Pro Thr Val Ser Pro Ala Pro Ala Asp Glu Pro Ser Ser Pro<br>740                     745                     750 | 2256 |
| ctg ctg tcc cct ggc tgc acc tcc tca tcc tca gct gcc aag ctg cta<br>Leu Leu Ser Pro Gly Cys Thr Ser Ser Ser Ser Ala Ala Lys Leu Leu<br>      755                     760                     765 | 2304 |
| tcc cca cgt cga aca gca ccc cgg cct cgt cta ggt ggc aga ggg agg<br>Ser Pro Arg Arg Thr Ala Pro Arg Pro Arg Leu Gly Gly Arg Gly Arg<br>770                     775                     780 | 2352 |
| cca ggc agg gca ggg gct ttg aag gct gag gct ggc ccc tct gct ccc<br>Pro Gly Arg Ala Gly Ala Leu Lys Ala Glu Ala Gly Pro Ser Ala Pro<br>785                     790                     795                     800 | 2400 |
| cca cgg gcc cta gag ggg cta cgg ctg ccc ccc atg cca tgg aat gtg<br>Pro Arg Ala Leu Glu Gly Leu Arg Leu Pro Pro Met Pro Trp Asn Val<br>                    805                     810                     815 | 2448 |
| ccc cca gat ctg agc ccc agg gta gta gat ggc att gaa gac ggc tgt<br>Pro Pro Asp Leu Ser Pro Arg Val Val Asp Gly Ile Glu Asp Gly Cys<br>820                     825                     830 | 2496 |
| ggc tcg gac cag ccc aag ttc tct ttc cgc gtg ggc cag tct ggc ccg<br>Gly Ser Asp Gln Pro Lys Phe Ser Phe Arg Val Gly Gln Ser Gly Pro<br>      835                     840                     845 | 2544 |
| gaa tgt agc agc agc ccc tcc cct gga cca gag agc ggc ctg ctc act<br>Glu Cys Ser Ser Ser Pro Ser Pro Gly Pro Glu Ser Gly Leu Leu Thr<br>850                     855                     860 | 2592 |
| gtt ccc cat ggg ccc agc gag gca agg aac aca gac aca ctg gac aag<br>Val Pro His Gly Pro Ser Glu Ala Arg Asn Thr Asp Thr Leu Asp Lys<br>865                     870                     875                     880 | 2640 |
| ctt cgg cag gcg gtg aca gag ctg tca gag cag gtg ctg cag atg cgg<br>Leu Arg Gln Ala Val Thr Glu Leu Ser Glu Gln Val Leu Gln Met Arg | 2688 |

-continued

| | | |
|---|---|---|
| gaa gga ctg cag tca ctt cgc cag gct gtg cag ctt gtc ctg gcg ccc<br>Glu Gly Leu Gln Ser Leu Arg Gln Ala Val Gln Leu Val Leu Ala Pro<br>900                     905                  910 | 2736 |
| cac agg gag ggt ccg tgc cct cgg gca tcg gga gag ggg ccg tgc cca<br>His Arg Glu Gly Pro Cys Pro Arg Ala Ser Gly Glu Gly Pro Cys Pro<br>915                     920                  925 | 2784 |
| gcc agc acc tcc ggg ctt ctg cag cct ctg tgt gtg gac act ggg gca<br>Ala Ser Thr Ser Gly Leu Leu Gln Pro Leu Cys Val Asp Thr Gly Ala<br>930                     935                  940 | 2832 |
| tcc tcc tac tgc ctg cag ccc cca gct ggc tct gtc ttg agt ggg act<br>Ser Ser Tyr Cys Leu Gln Pro Pro Ala Gly Ser Val Leu Ser Gly Thr<br>945                  950                  955                  960 | 2880 |
| tgg ccc cac cct cgt ccg ggg cct cct ccc ctc atg gca ccc tgg ccc<br>Trp Pro His Pro Arg Pro Gly Pro Pro Pro Leu Met Ala Pro Trp Pro<br>965                     970                  975 | 2928 |
| tgg ggt ccc cca gcg tct cag agc tcc ccc tgg cct cga gcc aca gct<br>Trp Gly Pro Pro Ala Ser Gln Ser Ser Pro Trp Pro Arg Ala Thr Ala<br>980                     985                  990 | 2976 |
| ttc tgg acc tcc acc tca gac tca gag ccc cct gcc tca gga gac ctc<br>Phe Trp Thr Ser Thr Ser Asp Ser Glu Pro Pro Ala Ser Gly Asp Leu<br>995                     1000                 1005 | 3024 |
| tgc tct gag ccc agc acc cct gcc tcc cct cct cct tct gag gaa<br>Cys Ser Glu Pro Ser Thr Pro Ala Ser Pro Pro Pro Ser Glu Glu<br>1010                   1015                 1020 | 3069 |
| ggg gct agg act ggg ccc gca gag cct gtg agc cag gct gag gct<br>Gly Ala Arg Thr Gly Pro Ala Glu Pro Val Ser Gln Ala Glu Ala<br>1025                   1030                 1035 | 3114 |
| acc agc act gga gag ccc cca cca ggg tca ggg ggc ctg gcc ttg<br>Thr Ser Thr Gly Glu Pro Pro Pro Gly Ser Gly Gly Leu Ala Leu<br>1040                   1045                 1050 | 3159 |
| ccc tgg gac ccc cac agc ctg gag atg gtg ctt att ggc tgc cat<br>Pro Trp Asp Pro His Ser Leu Glu Met Val Leu Ile Gly Cys His<br>1055                   1060                 1065 | 3204 |
| ggc tct ggc aca gtc cag tgg acc cag gaa gaa ggc aca ggg gtc<br>Gly Ser Gly Thr Val Gln Trp Thr Gln Glu Glu Gly Thr Gly Val<br>1070                   1075                 1080 | 3249 |
| tga | 3252 |

<210> SEQ ID NO 2
<211> LENGTH: 1083
<212> TYPE: PRT
<213> ORGANISM: Homo sapiens

<400> SEQUENCE: 2

Met Pro Ala Met Arg Gly Leu Leu Ala Pro Gln Asn Thr Phe Leu Asp
1                 5                   10                  15

Thr Ile Ala Thr Arg Phe Asp Gly Thr His Ser Asn Phe Val Leu Gly
            20                   25                   30

Asn Ala Gln Val Ala Gly Leu Phe Pro Val Val Tyr Cys Ser Asp Gly
                35                   40                   45

Phe Cys Asp Leu Thr Gly Phe Ser Arg Ala Glu Val Met Gln Arg Gly
50                   55                   60

Cys Ala Cys Ser Phe Leu Tyr Gly Pro Asp Thr Ser Glu Leu Val Arg
65                 70                   75                   80

Gln Gln Ile Arg Lys Ala Leu Asp Glu His Lys Glu Phe Lys Ala Glu
                  85                   90                   95

Leu Ile Leu Tyr Arg Lys Ser Gly Leu Pro Phe Trp Cys Leu Leu Asp

-continued

```
                100                 105                 110
        Val Ile Pro Ile Lys Asn Glu Lys Gly Glu Val Ala Leu Phe Leu Val
                    115                 120                 125
        Ser His Lys Asp Ile Ser Glu Thr Lys Asn Arg Gly Pro Asp Arg
                    130                 135             140
        Trp Lys Glu Thr Gly Gly Arg Arg Tyr Gly Arg Ala Arg Ser
        145                 150                 155                 160
        Lys Gly Phe Asn Ala Asn Arg Arg Ser Arg Ala Val Leu Tyr His
                        165                 170                 175
        Leu Ser Gly His Leu Gln Lys Gln Pro Lys Gly Lys His Lys Leu Asn
                    180                 185                 190
        Lys Gly Val Phe Gly Glu Lys Pro Asn Leu Pro Glu Tyr Lys Val Ala
                    195                 200                 205
        Ala Ile Arg Lys Ser Pro Phe Ile Leu Leu His Cys Gly Ala Leu Arg
                    210                 215                 220
        Ala Thr Trp Asp Gly Phe Ile Leu Leu Ala Thr Leu Tyr Val Ala Val
        225                 230                 235                 240
        Thr Val Pro Tyr Ser Val Cys Val Ser Thr Ala Arg Glu Pro Ser Ala
                        245                 250                 255
        Ala Arg Gly Pro Pro Ser Val Cys Asp Leu Ala Val Glu Val Leu Phe
                    260                 265                 270
        Ile Leu Asp Ile Val Leu Asn Phe Arg Thr Thr Phe Val Ser Lys Ser
                    275                 280                 285
        Gly Gln Val Val Phe Ala Pro Lys Ser Ile Cys Leu His Tyr Val Thr
                    290                 295                 300
        Thr Trp Phe Leu Leu Asp Val Ile Ala Ala Leu Pro Phe Asp Leu Leu
        305                 310                 315                 320
        His Ala Phe Lys Val Asn Val Tyr Phe Gly Ala His Leu Leu Lys Thr
                        325                 330                 335
        Val Arg Leu Leu Arg Leu Leu Arg Leu Leu Pro Arg Leu Asp Arg Tyr
                    340                 345                 350
        Ser Gln Tyr Ser Ala Val Val Leu Thr Leu Leu Met Ala Val Phe Ala
                    355                 360                 365
        Leu Leu Ala His Trp Val Ala Cys Val Trp Phe Tyr Ile Gly Gln Arg
                    370                 375                 380
        Glu Ile Glu Ser Ser Glu Ser Glu Leu Pro Glu Ile Gly Trp Leu Gln
        385                 390                 395                 400
        Glu Leu Ala Arg Arg Leu Glu Thr Pro Tyr Tyr Leu Val Gly Arg Arg
                        405                 410                 415
        Pro Ala Gly Gly Asn Ser Ser Gly Gln Ser Asp Asn Cys Ser Ser Ser
                    420                 425                 430
        Ser Glu Ala Asn Gly Thr Gly Leu Glu Leu Leu Gly Pro Ser Leu
                    435                 440                 445
        Arg Ser Ala Tyr Ile Thr Ser Leu Tyr Phe Ala Leu Ser Ser Leu Thr
                    450                 455                 460
        Ser Val Gly Phe Gly Asn Val Ser Ala Asn Thr Asp Thr Glu Lys Ile
        465                 470                 475                 480
        Phe Ser Ile Cys Thr Met Leu Ile Gly Ala Leu Met His Ala Val Val
                        485                 490                 495
        Phe Gly Asn Val Thr Ala Ile Ile Gln Arg Met Tyr Ala Arg Arg Phe
                    500                 505                 510
        Leu Tyr His Ser Arg Thr Arg Asp Leu Arg Asp Tyr Ile Arg Ile His
                    515                 520                 525
```

-continued

```
Arg Ile Pro Lys Pro Leu Lys Gln Arg Met Leu Glu Tyr Phe Gln Ala
    530                 535                 540
Thr Trp Ala Val Asn Asn Gly Ile Asp Thr Thr Glu Leu Leu Gln Ser
545                 550                 555                 560
Leu Pro Asp Glu Leu Arg Ala Asp Ile Ala Met His Leu His Lys Glu
                565                 570                 575
Val Leu Gln Leu Pro Leu Phe Glu Ala Ala Ser Arg Gly Cys Leu Arg
            580                 585                 590
Ala Leu Ser Leu Ala Leu Arg Pro Ala Phe Cys Thr Pro Gly Glu Tyr
        595                 600                 605
Leu Ile His Gln Gly Asp Ala Leu Gln Ala Leu Tyr Phe Val Cys Ser
    610                 615                 620
Gly Ser Met Glu Val Leu Lys Gly Gly Thr Val Leu Ala Ile Leu Gly
625                 630                 635                 640
Lys Gly Asp Leu Ile Gly Cys Glu Leu Pro Arg Arg Glu Gln Val Val
                645                 650                 655
Lys Ala Asn Ala Asp Val Lys Gly Leu Thr Tyr Cys Val Leu Gln Cys
            660                 665                 670
Leu Gln Leu Ala Gly Leu His Asp Ser Leu Ala Leu Tyr Pro Glu Phe
        675                 680                 685
Ala Pro Arg Phe Ser Arg Gly Leu Arg Gly Glu Leu Ser Tyr Asn Leu
    690                 695                 700
Gly Ala Gly Gly Gly Ser Ala Glu Val Asp Thr Ser Ser Leu Ser Gly
705                 710                 715                 720
Asp Asn Thr Leu Met Ser Thr Leu Glu Glu Lys Glu Thr Asp Gly Glu
                725                 730                 735
Gln Gly Pro Thr Val Ser Pro Ala Pro Ala Asp Glu Pro Ser Ser Pro
            740                 745                 750
Leu Leu Ser Pro Gly Cys Thr Ser Ser Ser Ala Ala Lys Leu Leu
        755                 760                 765
Ser Pro Arg Arg Thr Ala Pro Arg Pro Arg Leu Gly Gly Arg Gly Arg
    770                 775                 780
Pro Gly Arg Ala Gly Ala Leu Lys Ala Glu Ala Gly Pro Ser Ala Pro
785                 790                 795                 800
Pro Arg Ala Leu Glu Gly Leu Arg Leu Pro Pro Met Pro Trp Asn Val
                805                 810                 815
Pro Pro Asp Leu Ser Pro Arg Val Val Asp Gly Ile Glu Asp Gly Cys
            820                 825                 830
Gly Ser Asp Gln Pro Lys Phe Ser Phe Arg Val Gly Gln Ser Gly Pro
        835                 840                 845
Glu Cys Ser Ser Ser Pro Ser Pro Gly Pro Glu Ser Gly Leu Leu Thr
    850                 855                 860
Val Pro His Gly Pro Ser Glu Ala Arg Asn Thr Asp Thr Leu Asp Lys
865                 870                 875                 880
Leu Arg Gln Ala Val Thr Glu Leu Ser Glu Gln Val Leu Gln Met Arg
                885                 890                 895
Glu Gly Leu Gln Ser Leu Arg Gln Ala Val Gln Leu Val Leu Ala Pro
            900                 905                 910
His Arg Glu Gly Pro Cys Pro Arg Ala Ser Gly Glu Gly Pro Cys Pro
        915                 920                 925
Ala Ser Thr Ser Gly Leu Leu Gln Pro Leu Cys Val Asp Thr Gly Ala
    930                 935                 940
```

| | | | | | | | | | | | |
|---|---|---|---|---|---|---|---|---|---|---|---|
|Ser|Ser|Tyr|Cys|Leu|Gln|Pro|Pro|Ala|Gly|Ser|Val|Leu|Ser|Gly|Thr|
|945| | | | |950| | | | |955| | | | |960|

Trp Pro His Pro Arg Pro Gly Pro Pro Leu Met Ala Pro Trp Pro
            965                 970                 975

Trp Gly Pro Pro Ala Ser Gln Ser Pro Trp Pro Arg Ala Thr Ala
        980                 985                 990

Phe Trp Thr Ser Thr Ser Asp Ser Glu Pro Pro Ala Ser Gly Asp Leu
        995                 1000                1005

Cys Ser Glu Pro Ser Thr Pro Ala Ser Pro Pro Ser Glu Glu
    1010                1015                1020

Gly Ala Arg Thr Gly Pro Ala Glu Pro Val Ser Gln Ala Glu Ala
    1025                1030                1035

Thr Ser Thr Gly Glu Pro Pro Pro Gly Ser Gly Gly Leu Ala Leu
    1040                1045                1050

Pro Trp Asp Pro His Ser Leu Glu Met Val Leu Ile Gly Cys His
    1055                1060                1065

Gly Ser Gly Thr Val Gln Trp Thr Gln Glu Glu Gly Thr Gly Val
    1070                1075                1080

<210> SEQ ID NO 3
<211> LENGTH: 40
<212> TYPE: DNA
<213> ORGANISM: Artificial Sequence
<220> FEATURE:
<223> OTHER INFORMATION: Primer

<400> SEQUENCE: 3
attcgacgtc gatctttttt ccgtaaactc aataccaggc                40

<210> SEQ ID NO 4
<211> LENGTH: 20
<212> TYPE: DNA
<213> ORGANISM: Mus sp.

<400> SEQUENCE: 4
gcgggcatca aggagtcaag                                      20

<210> SEQ ID NO 5
<211> LENGTH: 20
<212> TYPE: DNA
<213> ORGANISM: Mus sp.

<400> SEQUENCE: 5
ctcctgtccc tcccgttgac                                      20

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
acgcgtcgac ctgcccgtgc tcctgagtg                            29

<210> SEQ ID NO 7
<211> LENGTH: 29
<212> TYPE: DNA
<213> ORGANISM: Artificial Sequence
<220> FEATURE:
<223> OTHER INFORMATION: Primer -continued

```
<400> SEQUENCE: 7
acgcgtcgac ccaagctctg aaaaaccag                                29

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
ggggtaccgc ggccgcgggg atccagacat gataag                        36

<210> SEQ ID NO 9
<211> LENGTH: 20
<212> TYPE: DNA
<213> ORGANISM: Homo sapiens

<400> SEQUENCE: 9
cgaggcaagg aacacagaca                                          20

<210> SEQ ID NO 10
<211> LENGTH: 18
<212> TYPE: DNA
<213> ORGANISM: Homo sapiens

<400> SEQUENCE: 10
ggggctgcag gcagtagg                                            18

<210> SEQ ID NO 11
<211> LENGTH: 20
<212> TYPE: DNA
<213> ORGANISM: Homo sapiens

<400> SEQUENCE: 11
agtcacttcg ccaggctgtg                                          20

<210> SEQ ID NO 12
<211> LENGTH: 18
<212> TYPE: DNA
<213> ORGANISM: Homo sapiens

<400> SEQUENCE: 12
ggggctgcag gcagtagg                                            18
```

TRANSGENIC ANIMALS

TECHNICAL FIELD

This invention relates to a model animal to be used as an effective tool for screening a substance for antidementia, a substance to improve learning and memory or a substance for antianxiety, and a method for screening a novel substance for antidementia, substance to improve learning and memory or substance for antianxiety, which uses said model animal.

BACKGROUND OF THE INVENTION

Studies on the disorders in learning new information which occupies an important part of the mental activities of human and on the disorders in keeping and recalling already learned information are main themes for elucidating higher brain functions which have been regarded as the final frontier of life science. However, the cause for the disorders is unclear even at present and there are no sufficiently effective medicaments yet, so that early development of therapeutic drugs is greatly demanded. Even in the case of medicaments which have been reported to be effective in improving impairment in learning and memory of dementia patients to a certain degree, it has been pointed out that the duration of action is short and the clinically effective range is narrow (Feldman H. et al., (2001), Neurology, 57 (4), 613–20), that side effects such as hepatic toxicity and the like are generated (Summers W. K. et al., (1989), Lancet, 1 (8640), 729) and the like. In addition, for the purpose of finding an agent showing a useful therapeutic effect, it is necessary to take into consideration not only its in vitro efficacy but also in vivo bioavailability and transferring activity into the brain of the agent itself. Accordingly, the presence of a model animal which can be analyzed at individual level is essential for the elucidation of onset mechanism of the disease, prevention of onset of the disease or improvement of its pathologic condition, development of medicinal techniques for the treatment and of medicaments, and the like.

The transgenic mouse is expected as a method for displaying functions of genes in the living body for development of models for respective human diseases and development of various therapeutic drugs using these models. Including the c-myc oncogene-introduced transgenic mouse as a leukemia model which received a patent for a living life for the first time in the world (U.S. Pat. No. 5,087,571), various pathological model mice have been introduced, such as a prostatic hyperplasia mouse (U.S. Pat. No. 5,175,383), a diabetes mellitus-generating mouse (Japanese Patent 2771493), an Alzheimer'S disease model mouse (Games D. et al., (1995), Nature, 373 (6514), 523–7) and the like. Although many of the dementia-related transgenic animals represented by an APP transgenic show pathologic changes of dementia, it is difficult to detect impairment of learning and memory as a behavioral pattern in these animals, so that attempts have been made detect it by adding some factors such as aging and the like (Moran P. M. et al., (1995), Proc. Natl. Acad. Sci. USA, 92, 5341–5345; Hsiao K. et al., (1996), Science, 274, 99–102; Arendash G. W. et al., (2001), Brain Res., 891, 42–53). However, because preparation of such transgenic animals takes time, it was not practical to conveniently mass-prepare transgenic animals capable of detecting disorders of learning and memory as a behavioral pattern for use in the screening of a substance for antidementia.

Accordingly, demands have been directed toward a model animal to be used as an effective tool for screening a substance for antidementia or a substance to improve learning and memory, and a method for screening a substance for antidementia or a substance to improve learning and memory, which uses said model animal.

On the other hand, anxiety is a physiological phenomenon functioning as a warning against a present or potential danger. Anxiety becomes pathologic when it occurs without a real danger or its emotional strength intensifies. It is known that both of the physiological and pathological anxieties can threaten life when an organ disorder is generated in spite of its previous presence and may cause or permanently keep various physiological dysfunctions. There are various reports on transgenic animals as models of anxiety (Holmes A., (2001), Neurosci. Biobehav. Rev., 25 (3), 261–73). However, there is no applicable and optimum agent having less side effects even now.

Regarding a potassium channel BEC1 which can be used in preparing the transgenic animal of the present invention, the present inventors have disclosed it in WO 99/37677, and there are many reports regarding polynucleotides and polypeptides having a homology of from 98 to 99% with the BEC1 (WO 00/05346, WO 00/09534, WO 99/43696). However, a BEC1 transgenic animal was not prepared in reality, and its functions were not necessarily understood completely.

DISCLOSURE OF THE INVENTION

As a result of extensive studies, the present inventors have succeeded in preparing a transgenic mouse over-expressing the potassium channel BEC1 (Miyake A. et al., (1999), J. Biol. Chem., 274, 25018–25025) and found that, since the learning and memory abilities of said transgenic mouse is reduced, it can be used as a tool for screening a substance for antidementia or a substance to improve learning and memory. Also, it was found unexpectedly that, since anxiety of said transgenic mouse is accelerated, it can be used as a tool for screening a substance for antianxiety. In addition, an in vivo screening system for a substance for antidementia or a substance to improve learning and memory was constructed using the learning and memory abilities of said transgenic mouse as the index, and an in vivo screening system for a substance for antianxiety using the anxiety of said transgenic mouse as the index. As the results, the present invention was accomplished by providing a BEC1 transgenic animal as a model animal to be used as an effective tool for screening a substance for antidementia, a substance to improve learning and memory or a substance for antianxiety, and a method for screening a substance for antidementia, a substance to improve learning and memory or a substance for antianxiety, which uses said transgenic animal.

Accordingly, the present invention relates to, (1) a transgenic animal introduced with a sequence comprising a promoter and a polynucleotide encoding a potassium channel which is a polypeptide consisting of the amino acid sequence represented by SEQ ID NO:2 or a polypeptide comprising an amino acid sequence in which from 1 to 10 of amino acids in the amino acid sequence represented by SEQ ID NO:2 are deleted, substituted and/or added, (2) a transgenic animal which is a non-human animal or a offspring animal thereof obtained by effecting ontogenesis of a totipotent cell introduced, together with a promoter, with a polynucleotide encoding a potassium channel which is a polypeptide consisting of the amino acid sequence represented by SEQ ID NO:2 or a polypeptide comprising an amino acid sequence in which from 1 to 10 of amino acids in the amino acid sequence represented by SEQ ID NO:2 are deleted substituted and/or added, characterized in that the aforementioned polynucleotide is held on the chromosome and expresses said potassium channel in somatic cells, (3) the transgenic animal described in (1) or (2), wherein it is obtained by effecting ontogenesis of a totipotent cell introduced, together with a promoter, with a polynucleotide encoding a potassium channel which is a polypeptide consisting of the amino acid sequence represented by SEQ ID NO:2 or a polypeptide which comprising an amino acid sequence in which from 1 to 10 of amino acids in the amino acid sequence represented by SEQ ID NO:2 are deleted substituted and/or added and is expressed limitedly to the brain, (4) a transgenic animal introduced with a sequence comprising a promoter and a polynucleotide encoding a polypeptide which consists of an amino acid sequence having a homology of 90% or more with the amino acid sequence represented by SEQ ID NO:2 and is a potassium channel, or a offspring animal thereof obtained by effecting ontogenesis of a totipotent cell introduced, together with a promoter, with a polynucleotide encoding a polypeptide which consists of an amino acid sequence having a homology of 90% or more with the amino acid sequence represented by SEQ ID NO:2 and is a potassium channel, characterized in that the aforementioned polynucleotide is held on the chromosome and expresses said potassium channel in somatic cells, (6) the transgenic animal described in (4) or (5), wherein it is obtained by effecting ontogenesis of a totipotent cell introduced, together with a promoter, with a polynucleotide encoding a potassium channel which is a polypeptide consisting of an amino acid sequence having a homology of 90% or more with the amino acid sequence represented by SEQ ID NO:2 and is expressed limitedly to the brain, (7) the transgenic animal described in (1) to (6), wherein the promoter is a promoter capable of effecting expression of the potassium channel limitedly to the brain, (8) the transgenic animal described in (1) to (7), wherein the promoter is an α-calcium-calmodulin-dependent kinase II promoter, (9) the transgenic animal described in (1) to (8), wherein the non-human animal is a mouse, (10), a method for detecting whether or not a substance to be tested inhibits said potassium channel, characterized in that it comprises
a step of administering a substance to be tested to the transgenic animal described in (1) to (9), and
a step of measuring learning and memory abilities, (11) a method for detecting whether or not a substance to be tested inhibits said potassium channel, characterized in that it comprises
a step of administering a substance to be tested to the transgenic animal described in (1) to (9), and
a step of measuring anxiety, (12) a method for detecting an anti-dementia effect or an improving effect on learning and memory, characterized in that it comprises
a step of administering a substance to be tested to the transgenic animal described in (1) to (9), and
a step of measuring learning and memory abilities, (13) a method for detecting an anxiety inhibiting effect, characterized in that it comprises
a step of administering a substance to be tested to the transgenic animal described in (1) to (9), and
a step of measuring anxiety, (14) a method for screening a substance for antidementia or a substance to improve learning and memory, characterized in that it comprises
a step of administering a substance to be tested to the transgenic animal described in (1) to (9), a step of measuring learning and memory abilities, and
a step of selecting a substance having an anti-dementia effect or an improving effect on learning and memory, (15) a method for screening a substance for antianxiety, characterized in that it comprises
a step of administering a substance to be tested to the transgenic animal described in (1) to (9), a step of measuring anxiety, and
a step of selecting a substance having an anxiety inhibiting effect, (16) a process for producing a pharmaceutical composition for antidementia or for improvement and therapy in learning and memory, characterized in that it comprises a step of carrying out screening using the screening method described in (14) and a step of making a pharmaceutical preparation using a substance obtained by the aforementioned screening, and (17) a process for producing a pharmaceutical composition for anti-anxiety action, characterized in that it comprises a step of carrying out screening using the screening method described in (15) and a step of making a pharmaceutical preparation using a substance obtained by the aforementioned screening.

Though there are many reports regarding polynucleotides and polypeptides having a homology of from 98 to 99% with the BEC1 which can be used in preparing the transgenic animal of the present invention (WO 00/05346, WO 00/09534, WO 99/43696), distinct use has not been elucidated for each of them. Also, though there are descriptions regarding transgenic animals in the aforementioned WO 00/05346 and WO 99/43696, their illustrative preparation methods are not described and there are no examples showing their actual preparation and no descriptions which support functions of said animals. On the other hand, the present inventors have disclosed on the BEC1 in WO 99/37677 in addition to the aforementioned pamphlets, but without descriptions regarding transgenic animals.

That is, the BEC1 transgenic animal, the method for screening a substance for antidementia, a substance to improve learning and memory and/or a substance for antianxiety, which uses said model animal, and the method for producing a pharmaceutical composition for antidementia, for improvement of learning and memory and/or antianxiety, described in the instant application, are inventions accomplished for the first time by the present inventors.

Regarding most of the transgenic animals other than the BEC1 counterpart, which have so far been reported on their ability to show a behavioral pattern of impairment in learning and memory, it was necessary to add some factors such as aging and the like for the detection of the disorders (Moran P. M. et al., (1995), *Proc. Natl. Acad. Sci. USA*, 92, 5341–5345; Hsiao K. et al., (1996), *Science*, 274, 99–102; Arendash G. W. et al., (2001), *Brain Res.*, 891, 42–53), but preparation of such transgenic animals costs and takes time, and it was not practical to conveniently mass-prepare and use a transgenic animal capable of detecting impairment in learning and memory as a behavioral pattern for use in the screening of a substance for antidementia. Since the BEC1 transgenic animal described in the instant application shows a behavior of impairment in learning and memory at a young stage, it can be prepared conveniently and at a low cost and used in the screening of a substance for antidementia.

BEST MODE FOR CARRYING OUT THE INVENTION

The terms to be used in the present invention are described.

The term "potassium channel" as used herein means a "potassium channel protein", and the term "BEC1" means a "BEC1 protein". The term "learning" as used herein means to acquire information from the external world, and the term "memory" includes preservation and regeneration of the information acquired by the leaning, and the process. The term "learning and memory" shows both concepts of "learning" and "memory", and the term "memorizing and learning ability" means the ability to acquire, preserve and regenerate the outside information.

The term "transgene" means a gene for transgenic animal preparation use, which contains a polynucleotide encoding a promoter region and a potassium channel.

The following describes the present invention in detail.

[1] Polynucleotide Contained in the Transgene for Use in the Preparation of the Transgenic Animal of the Present Invention and Polypeptide Encoded by Said Polynucleotide The potassium channel polypeptide encoded by the polynucleotide contained in the transgene for use in the preparation of the transgenic animal of the present invention includes (1) a polypeptide consisting of the amino acid sequence represented by SEQ ID NO:2,
(2) a polypeptide comprising an amino acid sequence in which from 1 to 10 of amino acids in the amino acid sequence represented by SEQ ID NO:2 are deleted substituted and/or added and is a potassium channel (to be referred to as functionally equivalent modified one hereinafter), and
(3) a polypeptide which consists of an amino acid sequence having a homology of 90% or more with the amino acid sequence represented by SEQ ID NO:2 and is a potassium channel (to be referred to as homologous polypeptide hereinafter).

As the functionally equivalent modified one, "a polypeptide which comprising the amino acid sequence represented by SEQ ID NO:2 and is a potassium channel", "a polypeptide which consists of an amino acid sequence in which from 1 to 10, preferably 1 to 7, more preferably 1 to 5, of amino acids in the amino acid sequence represented by SEQ ID NO:2 are deleted substituted and/or inserted and is a potassium channel" or "a polypeptide which consists of an amino acid sequence in which from 1 to 10, preferably 1 to 7, more preferably 1 to 5, of amino acids in the amino acid sequence represented by SEQ ID NO:2 are deleted substituted and/or inserted and is a potassium channel which is expressed limitedly to the brain" is desirable, and the "polypeptide which comprising the amino acid sequence represented by SEQ ID NO:2 and is a potassium channel" is more desirable.

Though the homologous polypeptide is not particularly limited, with the proviso that it consists of an amino acid sequence having a homology of 90% or more with the amino acid sequence represented by SEQ ID NO:2 and is a potassium channel, it can consist of an amino acid sequence having a homology of preferably 95% or more, more preferably 98% or more, with the amino acid sequence represented by SEQ ID NO:2 and is preferably a potassium channel which is expressed limitedly to the brain. In this connection, the aforementioned term "homology" as used herein means a value obtained by using parameters prepared as default by Clustal program (Higgins and Sharp, *Gene*, 73, 237–244, 1998; Thompson et al., *Nucleic Acid Res.*, 22, 4673–4680, 1994) retrieval. The aforementioned parameters are as follows. As Pairwise Alignment Parameters, K tuple 1
Gap Penalty 3
Window 5
Diagonals Saved 5

The polypeptide encoded by the polynucleotide contained in the transgene for use in the preparation of the transgenic animal of the present invention has been described in the foregoing, and the polypeptide consisting of the amino acid sequence represented by SEQ ID NO:2, the functionally equivalent modified body thereof and the homologous polypeptide thereof are generally referred to as "learning and memory potassium channel". The "learning and memory potassium channel" represents a "learning and memory potassium channel protein". A protein as the polypeptide consisting of the amino acid sequence represented by SEQ ID NO:2 is called BEC1.

In addition, the polynucleotide having a nucleotide sequence encoding the learning and memory potassium channel may be any polynucleotide with the proviso that it is a polynucleotide consisting of a nucleotide sequence encoding a polypeptide represented by the amino acid sequence described in SEQ ID NO:2, a functionally equivalent modified body thereof or a homologous polypeptide thereof. It is preferably a polynucleotide consisting of a nucleotide sequence encoding the amino acid sequence described in SEQ ID NO:2, more preferably the nucleotide sequence described in SEQ ID NO:1.

[2] Method for Preparing Transgenic Animal Characterized in that it Expresses Learning and Memory Potassium Channel A polynucleotide encoding a learning and memory potassium channel contained in a transgene can be obtained in accordance with the method described in WO 99/37677. For example, the BEC1 gene described in SEQ ID NO:1 can be prepared by a method in which an oligonucleotide is synthesized based on a nucleotide sequence of an optional part of a known sequence (WO 99/37677), and a human cDNA library is screened using this as a probe, or by synthesizing an oligonucleotide which hybridizes with both termini of the cDNA fragment of interest, and preparing it by the reverse transcriptase-polymerase chain reaction (RT-PCR method) using this as a primer from mRNA isolated from a human cell. In addition, a promoter sequence and an enhancer sequence for controlling expression of the potassium channel are linked to the transgene. By selecting this promoter/enhancer sequence, said potassium channel can be systemically expressed and can be selectively expressed in a specified tissue. Regarding the promoter, though not particularly limited, the promoter region of an α-calcium-calmodulin-dependent kinase II (α-CaM-kinase II) gene (Mayford, M. et al. (1990), *Proc. Natl. Acad. Sci. USA*, 93, 13250–13255), the promoter region of a neuron-specific enolase (Quon, D. et al. (1991), *Nature*, 352, 239–241), the promoter region of a Thy-1 gene (Vidal, M. et al. (1990), *EMBO J.*, 9, 833–840) or the like can be used, the use of the promoter region of an α-calcium-calmodulin-dependent kinase II gene is desirable. Since the α-calcium-calmodulin-dependent kinase II gene is brain-selective and particularly it is a neuronal gene having high expression selectivity to the forebrain, a gene of interest can be expressed selectively in the brain, particularly in the forebrain (cerebral cortex and hippocampus), by the use of said promoter.

More illustratively, a transgene for use in the preparation of the transgenic animal of the present invention can be obtained by the method described in Example 1. As the transgene for use in the preparation of the transgenic animal of the present invention, a gene in which a BEC1 cDNA having a 5' intron and poly(A) addition signal is linked to a downstream of the promoter region of α-calcium-calmodulin-dependent kinase II gene can for example be cited. Though the production method of said transgene is not particularly limited, a method which uses the polymerase chain reaction (Saiki, R. K. et al. (1988), *Science*, 239, 487–491; to be referred to as PCR hereinafter) can for example be cited. In addition, the gene manipulation techniques of the present invention can be carried out in accordance with known methods (e.g., Maniatis, T. et al., "Molecular Cloning—A Laboratory Manual", Cold Spring Harbor Laboratory, NY, 1982).

Firstly, for the preparation of the promoter region of α-calcium-calmodulin-dependent kinase II gene, a set of primers, such as SEQ ID NO:3 and SEQ ID NO:4, which can amplify the DNA of the present invention are designed based on the information of each nucleotide sequence represented by a sequence (Accession No. AJ222796) registered in a gene data base GenBank.

A part of said transgene can be obtained by carrying out PCR using the thus designed aforementioned primer set and a genomic DNA as the template. As the genomic DNA, a commercially available product (mfd. by Clontech) can be used, or it can be obtained from an animal blood sample using a commercially available genomic DNA extraction kit (mfd. by QIAGEN). In addition, α-calcium-calmodulin-dependent kinase II promoter region can be obtained by integrating the thus obtained DNA into an appropriate vector.

On the other hand, the polynucleotide encoding said potassium channel can be obtained in the following manner, it is not limited to this method and can be obtained also by the method described in WO 99/37677.

A mRNA sample including the one encoding said potassium channel is extracted by a known method from a cell or tissue, for example, the human brain, having an ability to produce said potassium channel. As the extraction method, the guanidine thiocyanate hot phenol method, the guanidine thiocyanate-guanidine hydrochloride method and the like can be exemplified, but the guanidine thiocyanate cesium chloride method can be cited as a desirable method. The cell or tissue having the ability to produce said potassium channel can be specified by a northern blotting method which uses a gene having a nucleotide sequence encoding said potassium channel or a part thereof or a western blotting method which uses an antibody specific for said potassium channel.

Purification of the mRNA can be carried out in accordance with a conventional method; for example, it can be purified by effecting adsorption of the mRNA to an oligo (dT) cellulose column and then eluting the same. As occasion demands, the mRNA can be further fractionated by a sucrose density gradient centrifugation or the like method. In addition, a commercially available already extracted mRNA can also be used without carrying out extraction of the mRNA.

Next, a single-stranded cDNA is synthesized by carrying out a reverse transcriptase reaction of the thus purified mRNA in the presence of a random primer or an oligo(dT) primer. This synthesis can be carried out by a conventional method. The potassium channel DNA of interest is amplified by carrying out PCR using the thus obtained single-stranded cDNA and two primers sandwiching a partial region of the gene of interest. The thus obtained DNA is fractionated by an agarose gel electrophoresis or the like. As occasion demands, a DNA fragment of interest can also be obtained by digesting the aforementioned DNA with restriction enzymes and the like and ligating the fragments.

Regarding the transgene for use in the preparation of the transgenic animal of the present invention, the arrangment order of the polynucleotides encoding the promoter and the learning and memory potassium channel is not particularly limited, as long as it contains at least an arbitrary promoter region and a polynucleotide encoding the learning and memory potassium channel, and the polynucleotide encoding the learning and memory potassium channel is arranged in such a manner that it is set under control of the promoter activity. As described in Example 1, the transgene for use in the preparation of the transgenic animal of the present invention can be prepared by transferring the aforementioned promoter region and the learning and memory potassium channel gene successively to multi-cloning sites of an appropriate vector. As the aforementioned vector, pUC18 (mfd. by Toyobo) can for example be cited.

The transgenic animal of the present invention is not particularly limited, as long as said transgene is introduced and the learning and memory potassium channel is overexpressed, but it can be prepared, for example, based on a conventionally known method (e.g., *Animal Biotechnology*, 1, 175–84, 1990) except that said transgene is used as the gene to be introduced. Illustratively, it can be prepared based, for example, on the procedure described in Example 1 which is described later. That is, a transgenic animal of interest can be prepared by introducing the aforementioned transgene into a totipotent cell of a non-human animal, allowing this cell to develop into individuals and then selecting an individual in which the transgene is integrated into the genome of somatic cell. The term "animal" as used herein means an animal excluding human (namely, non-human animal), and its examples include mammals other than human (e.g., rat, mouse, dog, cat, monkey, pig, cattle, sheep, rabbit, goat, dolphin or horse), birds (e.g., domestic fowl or quail), the amphibia (e.g., frog), the reptiles, insects (e.g., *Drosophila*) and the like. As the non-human animal, technically it is possible to use all animal species, but a mouse is particularly desirable, because a large number of inbred strains are created and, what is more, fertilized egg culturing, in vitro fertilization and the like techniques are well established. As the totipotent cell into which a gene is introduced, a fertilized egg or early stage embryo can be used in the case of mouse. In addition, physical injection (microinjection) of DNA is desirable as the method for introducing the gene into a cultured cell, when the production efficiency of transgenic animal individuals and the transferring efficiency of the transgene to the next generation are taken into consideration.

For example, a vector dissolved in HEPES buffer, phosphate buffer, physiological saline or the like is injected into a fertilized egg, and this egg is transplanted into the womb of a host animal treated with a hormone ($PGF_2\alpha$, hCG, estradiol, LH or the like) or, in the case of a small animal, of an individual treated by a physical stimulation, for inducing into a condition of pseudopregnancy. By feeding this host animal and allowing it to carry out delivery, a gene-transferred non-human animal is obtained. Whether nor not a gene-transferred non-human animal is obtained can be known by extracting DNA from a part of the body (e.g., tail tip) and verifying the presence of the transgene by the Southern analysis or PCR. When an individual in which the presence of the transgene was confirmed is used as the founder, the transgene is transferred to 50% of its offspring, so that it is possible to prepare a wild type or mutation type animal efficiently.

The transgenic animal prepared in this manner is useful for a method for screening an agent targeted said channel, a method for detecting an anti-dementia effect or learning and memory improving effect, a method for detecting an anxiety inhibitory effect, a method for screening a substance for antidementia or a substance to improve learning and memory, and a method for screening a substance for anti-anxiety.

Although the substance to be tested which is used in the screening method of the present invention is not particularly limited, its examples include commercially available compounds (including peptides), various conventionally known compounds (including peptides) registered in Chemical File, a group of compounds obtained by the combinatorial chemistry techniques (N. K. Terrett, M. Gardner, D. W. Gordon, R. J. Kobylecki and J. Steele, *Tetrahedron*, 51, 8135–37, (1995)), microbial culture supernatants, natural components derived from plants and marine organisms, animal tissue extracts, and compounds (including peptides) prepared by chemically or biologically modifying the compounds (including peptides) selected by the screening method of the present invention.

[3] Method for Measuring Memorizing and Learning Ability and Method for Detecting (Screening) Substance to Improve Learning and Memory The method for measuring memorizing and learning ability and method for detecting (screening) substance to improve learning and memory are described in the following. By the following methods for measuring memorizing and learning ability, whether or not a compound to be tested inhibits the learning and memory potassium channel can be detected.

1. A Method which Uses a Passive Avoidance Test

The anti-dementia effect and improvement effect on learning and memory can be detected through the measurement of the memorizing and learning ability by a passive avoidance test. The passive avoidance test can be carried out according to McGaugh J. L. (1966), *Science*, 153, 1351–1358, more illustratively by the method described in Example 5. Each compound to be tested is administered before the start of training (e.g., before 15 to 30 minutes) on the first day of the test. When the latency to enter the dark box of the test compound-administered group is prolonged in comparison with the vehicle-administered group, it can be judged that the compound has an anti-dementia effect or a learning and memory improvement effect. The test compound having an anti-dementia effect or a learning and memory improvement effect can be selected as a substance for antidementia or a substance to improve learning and memory. In this connection, the vehicle-administered group means a group to which the vehicle of test compound (e.g., 0.5% methyl cellulose physiological saline or the like) alone was administered.

2. A Method Which Uses a Morris Water Maze Test

The anti-dementia effect and learning and memory improvement effect can be detected through the measurement of the memorizing and learning ability by a method which uses a Morris water maze test. This can be carried out as described in Example 4 in accordance with the method of Wenk G L et al. (1997), Learning and Memory. In Current Protocols in Neuroscience, New York, pp.8.5A. 1–8.5B. 7. Each compound to be tested is administered before the training (e.g., before 0 to 30 minutes) on each day. When the escepe latency to the platform in the test compound-administered group on and after the 2nd day is shortened in comparison with the vehicle-administered group, it can be judged that the compound has an anti-dementia effect or a learning and memory improvement effect. The test compound having an anti-dementia effect or a learning and memory improvement effect can be selected as a substance for antidementia or a substance to improve learning and memory.

3. A Method which Uses a Sound-clued Fear Conditioning

The anti-dementia effect and learning and memory improvement effect can be detected through the measurement of the memorizing and learning ability by a method which uses a sound-clued fear conditioning. This can be carried out in accordance with the method of Wehner J M et al. (1997), *Nature Genetics*, 17, 331–334. A sound stimulus (5 kHz for 10 seconds) is produced to a transgenic mouse and a constant current stimulus (0.5 mA for 1 second) is added immediately thereafter. Each compound to be tested is administered 30 minutes before the provision of sound and electricity stimuli. After 24 hours, the sound stimulus alone is produced to the mouse, and freezing time of the mouse is measured for 5 minutes. When the immovable period of time is prolonged in comparison with the vehicle-administered group, it can be judged that the compound has an anti-dementia effect or a learning and memory improvement effect. The test compound having an anti-dementia effect or a learning and memory improvement effect can be selected as-a substance for antidementia or a substance to improve learning and memory.

4. A Method which Uses Object Recognition Task

The anti-dementia effect and learning and memory improvement effect can be detected through the measurement of the memorizing and learning ability by a method which uses an object recognition task. This can be carried out in accordance with the method of Ennaceur A and Delacour J (1988), *Behavior Brain Research*, 31, 47–59. After standing still two identical objects inside a 60 cm square field, a transgenic mouse is put into the field and allowed to make a search inside the field freely for 5 minutes. Each test compound is administered 1 hour before putting the mouse into the field. One hour thereafter, one of the two objects is replaced by a different new object, and the mouse is again allowed to make a search inside the field for 5 minutes. A difference between the searching time for the new object and the searching time for the old object is used as the index of memory retention, and when this difference is prolonged in the test compound-administered group, it can be judged that the compound has an anti-dementia effect or a learning and memory improvement effect. The test compound having an anti-dementia effect or a learning and memory improvement effect can be selected as a substance for antidementia or a substance to improve learning and memory.

5. A Method which Uses an Eyeblink Conditioning

The anti-dementia effect and learning and memory improvement effect can be detected through the measurement of the memorizing and learning ability by a method which uses an eyeblink conditioning. The mouse eyeblink conditioning can be carried out in accordance with the method of Chen L et al. (1996), *Journal of Neuroscience*, 16, 2829–2838. An electrode is embedded into the eyelid muscle of a transgenic mouse to record electromyogram of the eyelid muscle. A sound stimulus (5 kHz for 2 seconds) is produced to the mouse and an electric stimulus is added immediately thereafter from the embedded electrode to induce a blink in the mouse. The sound-electric stimuli are produced 50 times a day, and this training is carried out continuously 7 days. Each compound to be tested is administered every day 1 hour before the provision of stimuli. The frequency of generation of the eyelid muscle activity after the sound stimulus provision and before the electric stimulus provision is used as the index of the conditioned memory acquisition. When the frequency of generation of the eyelid muscle activity in the test compound-administered group exceeds that of the vehicle-administered group on and after the 2nd day of the start of the training, it can be judged that the compound has an anti-dementia effect or a learning and memory improvement effect. The test compound having an anti-dementia effect or a learning and memory improvement effect can be selected as a substance for antidementia or a substance to improve learning and memory.

6. A Method which Uses Long-term Potentiation (LTP) in Hippocampus CA1 as the Index The anti-dementia effect and learning and memory improvement effect can be detected through the measurement of the memorizing and learning ability by a method which uses long-term potentiation (LTP) in hippocampus CA1 as the index. The LTP in hippocampus CA1 can be carried out according to Tsien, J Z et al. (1996), *Cell*, 87, 1327–1338 or Oka H et al. (1999), *J. Neurosci. Methods*, 93, 61–67 or the like, more illustratively by the method described in Example 7. Each compound to be tested is applied before the tetanus stimulation (e.g., before 15 to 30 minutes). When the LTP at the time of the test compound addition is accelerated in comparison with the case of the vehicle addition, it can be judged that the compound has an anti-dementia effect or a learning and memory improvement effect. The test compound having an anti-dementia effect or a learning and memory improvement effect can be selected as a substance for antidementia or a substance to improve learning and memory.

[4] Measuring Method of Anxiety and Detection Method of Substance for Antianxiety Measuring method of anxiety and detection method of a substance for antianxiety are exemplified in the following. By the following anxiety measuring methods, whether or not a compound to be tested inhibits the learning and memory potassium channel can be detected.

1. A Method which Uses a Light/Dark Exploration Test

The anxiety controlling effect can be detected through the measurement of anxiety by a method which uses a light/dark exploration test. This can be carried out as described in Example 6 in accordance with the method of Crawly J N et al. (1997), Current Protocols in Neuroscience, Wiley, New York. Administration of each compound to be tested is carried out 30 minutes before the start of the test. When the time spent in the light box or number of transitions between the light and dark box in the test compound-administered group exceeds that of the vehicle-administered group, it can be judged that the compound has an anxiety controlling effect. The test compound having an anxiety controlling effect can be selected as a substance for antianxiety.

2. In addition to this, the anxiety controlling effect can be detected through the measurement of anxiety by a conflict test (Carlini et al., (1978), *Mod. Probl. Pharmacopsychiatry*, 13, 80–102), an elevated plus maze (Handley S L and Mithani S (1984), *Naunyn-schmiedeberg's Archive of Pharmacology*, 327, 1–5) and the like. When improvement is found in the scores by these methods after administration of a compound to be tested to a transgenic mouse, it can be judged that the compound has an anxiety controlling effect. The test compound having an anxiety controlling effect can be selected as a substance for antianxiety.

[5] Production Method of Pharmaceutical Composition for Anti-dementia, Learning and Memory Improvement and Treatment or Anti-anxiety Medicaments can be obtained using, as the main component, a substance capable of inhibiting the learning and memory potassium channel activity, which is selected by the screening method of the present invention. These medicaments are useful as a substance for antidementia, a substance to improve learning and memory or a substance for antianxiety.

The pharmaceutical preparation which contains a substance capable of inhibiting the learning and memory potassium channel activity as the active ingredient can be prepared by using carriers, fillers and/or other additive agents generally used in preparing medicaments, in response to the type of the active ingredient. Examples of the administration include oral administration by tablets, pills, capsules, granules, fine subtilaes, powders, solutions for oral use and the like and parenteral administration by intravenous, intramuscular or the like injections, suppositories, percutaneous preparations, transmucosal preparations and the like. Particularly in the case of peptides which are digested in the stomach, intravenous injection or the like parenteral administration is desirable.

The solid composition for oral administration according to the present invention can be prepared by mixing one or more active substances with at least one inert diluent such as lactose, mannitol, glucose, microcrystalline cellulose, hydroxypropylcellulose, starch, polyvinyl pyrrolidone, aluminum magnesium silicate or the like. In the usual way, the aforementioned solid composition may contain other additives than the inert diluent, such as a lubricant, a disintegrating agent, a stabilizing agent, a solubilizing agent, a solubilization assisting agent and the like. If necessary, tablets or pills may be coated with a sugar coating or a film of a gastric or enteric substance. The liquid composition for oral administration includes, for example, emulsions, solutions, suspensions, syrups or elixirs and can contain a generally used inert diluent such as purified water or ethanol. In addition to the inert diluent, the aforementioned liquid composition can contain other additive agent such as a moistening agent, a suspending agent, a sweetener, an aromatic or an antiseptic.

The injections for parenteral administration can include aseptic aqueous or non-aqueous solutions, suspensions or emulsions. As a diluent, the water-soluble aqueous solutions or suspensions can include distilled water for injection, physiological saline or the like. As the diluent of the non-aqueous solutions or suspensions, it can include, for example, plant oil (e.g., propylene glycol, polyethylene glycol or olive oil), alcohols (e.g., ethanol), polysorbate 80 or the like. The aforementioned composition can further contain a moistening agent, an emulsifying agent, a dispersing agent, a stabilizing agent, a solubilizing agent, a solubilization assisting agent, an antiseptic or the like. The aforementioned composition can be sterilized, for example, by filtration through a bacteria retaining filter, blending of a germicide or irradiation. Alternatively, it can be used by firstly making into a sterile solid composition and dissolving it in sterile water or a sterile solvent for injection prior to its use.

Dose of the medicament containing, as the active ingredient, a substance capable of inhibiting the learning and memory potassium channel activity, which is selected by the screening method of the present invention, can be optionally decided by taking into consideration strength of the activity of the active ingredient selected by the aforementioned screening method, and symptoms, age, sex and the like of each patient to be treated.

EXAMPLES

The following describes the present invention in detail based on examples, but the present invention is not restricted by said examples. In this connection, unless otherwise noted, gene manipulation techniques can be carried out in accordance with the conventionally known methods (Maniatis, T. et al. (1982): "Molecular Cloning—A Laboratory Manual", Cold Spring Harbor Laboratory, NY and the like). Also, when commercially available reagents and kits are used, they can be used in accordance with the instructions attached to the commercial products.

Example 1

Construction of Transgene for BEC1-overexpressing Transgenic Mouse

The transgene for production of a transgenic mouse overexpressing BEC1 having the amino acid sequence described in SEQ ID NO:2 comprises a gene in which a BEC1 cDNA (SEQ ID NO:1) with a 5' intron and poly(A) addition signal is linked to a downstream of the promoter region of α-calcium-calmodulin-dependent kinase II gene.

The promoter region of α-calcium-calmodulin-dependent kinase II was obtained as two fragments having a mutually overlapping region, by PCR using a C57BL/6 mouse genomic DNA as the template. The C57BL/6 mouse genomic DNA was purified from a blood sample of the same mouse using a genomic DNA extraction kit (QIAamp DNA Blood Midi Kit, mfd. by QIAGEN). Primers were designed based on the sequence registered in a gene data base GenBank (Accession No. AJ222796). A gene fragment of 4.6 kb was obtained using an oligonucleotide of the nucleotide sequence represented by SEQ ID NO:3 as the forward primer and using an oligonucleotide of the nucleotide sequence represented by SEQ ID NO:4 as the reverse primer. An AatII recognition sequence is added to the 5' terminal side of the aforementioned forward primer. In addition, a gene fragment of 3.7 kb was obtained using an oligonucleotide of the nucleotide sequence represented by SEQ ID NO:5 as the forward primer and using an oligonucleotide of the nucleotide sequence represented by SEQ ID NO:6 as the reverse primer. A SalI recognition sequence is added to the 5' terminal side of the aforementioned reverse primer. Each PCR was carried out using a DNA polymerase (Pfu Turbo, mfd. by Stratagene) by employing a thermal denaturation at 99° C. (1 minute) and subsequent repetition of 45 cycles each comprising 99° C. (15 seconds), 58° C. (15 seconds) and 75° C. (10 minutes), or a thermal denaturation at 95° C. (1 minute) and subsequent repetition of 40 cycles each comprising 95° C. (15 seconds), 62° C. (15 seconds) and 75° C. (8 minutes), and the thus obtained gene fragment was cloned into a cloning vector (pCR-XL-TOPO plasmid, mfd. by Invitrogen). An endogenous XmaI recognizing sequence is present in the overlapping region of the 4.6 kb fragment and 3.7 kb fragment. The 4.6 kb fragment was digested with restriction enzymes AatII and XmaI, and the 3.7 kb fragment was digested with restriction enzymes XmaI and SalI. The thus obtained respective fragments were ligated and cloned into a plasmid pUC18 (mfd. by Toyobo) making use of the AatII and SalI recognition sequences. The α-calcium-calmodulin-dependent kinase II promoter region of interest was obtained by the above operation.

On the other hand, the BEC1 cDNA (SEQ ID NO:1) was obtained as a fragment containing a 5' intron and poly(A) addition signal by PCR using a potassium channel expression vector pME-E1 (described in WO 99/37677) as the template. An oligonucleotide of the nucleotide sequence represented by SEQ ID NO:7 was designed as the forward primer, and an oligonucleotide comprising the nucleotide sequence represented by SEQ ID NO:8 as the reverse primer, respectively from the upstream sequence of 5' intron and downstream sequence of poly(A) addition signal. A SalI recognition sequence is added to the aforementioned forward primer, and KpnI and NotI recognizing sequences to the reverse primer. PCR was carried out using a DNA polymerase (Pfu Turbo, mfd. by Stratagene) by employing a thermal denaturation at 96° C. (1 minute) and subsequent repetition of 30 cycles each comprising 96° C. (15 seconds), 60° C. (15 seconds) and 75° C. (8 minutes). The thus obtained 3.7 kb fragment was cloned into a cloning vector (pCR-XL-TOPO plasmid, mfd. by Invitrogen). This fragment was subcloned into a plasmid pUC18 (mfd. by Toyobo) making use of the SpeI recognition sequence and KpnI recognition sequence, and the aforementioned α-calcium-calmodulin-dependent kinase II promoter region was further subcloned into its upstream making use of the AatII recognition sequence and SalI recognition sequence. A plasmid (named pCM-E1 plasmid) having a transgene (12 kb) for use in the preparation of a BEC1-overexpressing transgenic mouse was finally obtained by the above operation.

Example 2

Preparation and Identification of BEC1 Over-expression Transgenic Mouse

The transgene (12 kb) for production. of a BEC1-overexpressing transgenic mouse was cut out from pCM-E1 using restriction enzymes AatII and NotI and then isolated and purified. The thus obtained gene was micro-injected into 283 fertilized eggs of F1 hybrid mice of C57BL/6 and DBA2 mice, and then the resulting fertilized eggs were transplanted into oviducts of ICR foster mother mice (Hogan, B. et al. (1986), Manipulating the mouse embryo: a laboratory manual, Plainview, N.Y.; Cold Harbor Press). The pregnant mice were allowed to undergo spontaneous delivery, and the thus obtained 81 offspring mice were subjected to the identification of transgenic mice.

Figure 1:
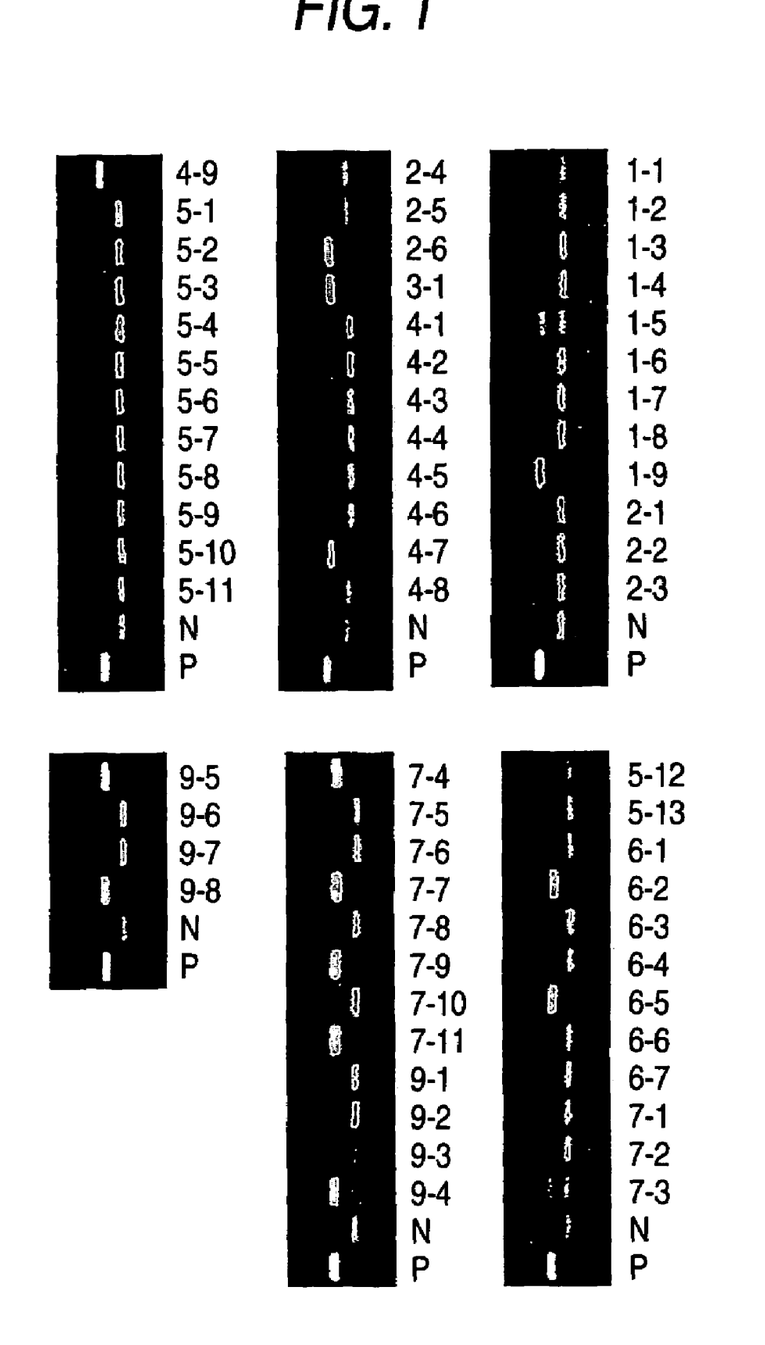
FIG. 1 is a graph showing a result of an electrophoresis of PCR products obtained by carrying out PCR using a genomic DNA as the template isolated from the tail of an infant mouse in order to identify the transgenic mouse. N indicate a negative control (mouse genomic DNA, 338 bp) and P indicate a positive control (transgene, 245 bp).

In order to identify transgenic mice, PCR was carried out using genomic DNA isolated from the tail of each offspring mouse as the template. The genomic DNA was purified from the tail of each mouse using a genomic DNA extraction kit (MagExtractor -Genome-, mfd. by Toyobo). When an oligonucleotide of the nucleotide sequence represented by SEQ ID NO:9 is designed as the forward primer, and an oligonucleotide of the nucleotide sequence represented by SEQ ID NO:10 as the reverse primer, from the BEC1 cDNA (SEQ ID NO:1), and PCR is carried out using them, a 245 bp fragment is amplified from the transgene, and a 338 bp fragment containing 93 bp intron of mouse BEC1 from the mouse genomic DNA. PCR was carried out on the thus obtained baby mouse genomic DNA preparations using these priers. PCR was carried out using a DNA polymerase (AmpliTaq, mfd. by Roche) by employing a thermal denaturation at 94° C. (1 minute) and subsequent repetition of 35 cycles each comprising 94° C. (15 seconds), 60° C. (15 seconds) and 72° C. (30 seconds). The PCR products were subjected to an agarose gel electrophoresis, and DNA was detected by ethidium bromide staining (FIG. 1). As a result, it was identified that 16 of the 81 baby mice are transgenic mice.

Example 3

Determination of BEC1 mRNA

In order to confirm that the introduced gene is actually functioning and BEC1 mRNA is over-expressing, expression of BEC1 mRNA in the brain of transgenic mouse was analyzed. In order to obtain F1 mice for brain extraction use, 11 animals among the 16 transgenic mice were crossed with C57BL/6 mice. As a result, transfer of the transgene to F1 mice was confirmed in 5 transgenic mice. The forebrain and cerebellum were sampled from each of the thus obtained F1 transgenic mice (4-week-old) to isolate respective RNA. Each RNA was digested with a DNase (mfd. by Promega) for the purpose of preventing contamination of genomic DNA. The number of copies of BEC1 mRNA in the thus obtained RNA was determined by a real time PCR using PRISM 7700 (mfd. by ABI) and a fluorescence reagent SYBR Green (mfd. by Molecular Probe). A single-stranded cDNA synthesized from each RNA using a reverse transcriptase-polymerase chain reaction kit (Advantage RT-for-PCR Kit, mfd. by Clontech) was used as the template of the real time PCR. An oligonucleotide of the nucleotide sequence represented by SEQ ID NO:11 was designed as the forward primer, and an oligonucleotide pf the nucleotide sequence represented by SEQ ID NO:12 as the reverse primer, from a sequence common to the transgene, human BEC1, and rat and mouse BEC1.

Figure 2:
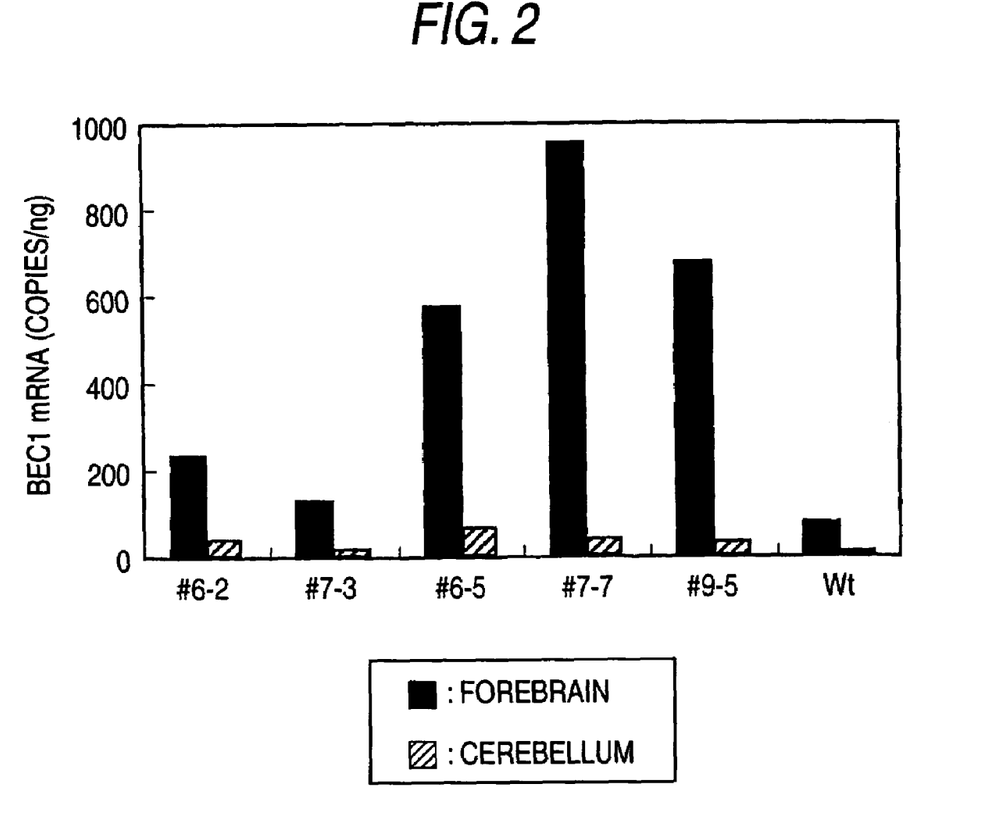
FIG. 2 is a graph showing expressed amounts of BEC1 mRNA in the forebrain and cerebellum of F1 transgenic mice (# 6-2, # 7-3, # 6-5, # 7-7 and # 9-5) and a wild type (Wt) mouse.

As a result of the real time PCR, over-expression of forebrain-selective BEC1 mRNA about 10 times higher than that of wild type was found in 3 lines (# 6-5, # 7-7 and # 9-5) among the 5 lines of transgenic mice (FIG. 2). By selecting the line # 9-5, expressed amounts of BEC1 mRNA in respective regions of the brain (cerebral cortex, hippocampus, striatum, hypothalamus, thalamus, mid-brain, brain stem, cerebellum) of wild type mouse were compared with those of the transgenic mouse. As a result, it was confirmed that the BEC1 mRNA over-expression in the transgenic mouse significant in cerebral cortex, hippocampus and striatum in which the expression was also found in the wild type.

Example 4

Analysis of Learned Behavior of BEC1-overexpressing Transgenic Mouse in a Morris Water Maze Test In order to analyze action of BEC1 overexpression upon learning behavior, learning behavior of # 9-5 line transgenic mice and that of wild type mice in a Morris water maze were compared.

Male 10-week-old transgenic mice (12 animals) and wild type mice (15 animals) were used. A circular pool of 100 cm in diameter was filled with water which had been clouded using paints, and a circular platform of 10 cm in diameter was arranged at a position of 5 mm below the water. Room temperature and water temperature at the time of the test was 23° C. Swimming pattern of each mouse put into the pool was recorded and analyzed by a water maze image analyzer (NIH image, mfd. by O'Hara & CO.), and the escape latency to the platform and the time spent in each quarter area of the pool were measured. One trial of the training was fixed to 70 seconds, and the training was carried out 3 trials per day for 5 days. The escape latency to the platform on the first day of the training was almost the same value in both groups, but the escape latency was prolonged in the transgenic mice than the wild type mice on and after the 3rd day of the start of the training. On the final day of the training, the escape latency to the platform (average value±standard deviation) became 6.9±1.0 seconds in the wild type and 18.1±6.4 seconds in the transgenic mice, thus showing a statistically significant difference ($p<0.05$: two-way layout analysis of variance).

After completion of the training, each mouse was put for 40 seconds into the pool from which the platform had been removed, and time of the mouse spent in the platform-existed area was measured. As a result, the spent time of transgenic mice was statistically significantly shorter than that of the wild type ($p<0.01$: Student's t test).

The above results show that learning and memory on the platform position are reduced in the transgenic mice. By this method which uses BEC1 transgenic mice, a substance for antidementia or a substance to improve learning and memory can be screened.

Example 5

Analysis of Learned Behavior of BEC1-overexpressing Transgenic Mouse in a Passive Avoidance Test Female # 9-5 line transgenic mice (6 animals) and wild type mice (8 animals), 8-week-old, were used. Each mouse was put into the light box region of a light and dark test apparatus for mice (mfd. by O'Hara & Co.), and a constant voltage stimulus of 60 V for 2 seconds was applied to the mouse when it entered the dark box. The mouse was again put into the light box 24 hours thereafter, and the latency to the dark box at this time was measured.

As a result, the latency to the dark box of the transgenic mice was 167 seconds (median) which was significantly short compared to the 600 seconds (median) of the wild type mice ($p<0.05$: Wilecoxon rank sum test). It was shown that the ability to learn the dark box-related electric stimulus is reduced in the transgenic mice. By this method which uses BEC1 transgenic mice, a substance for antidementia or a substance to improve learning and memory can be screened.

Example 6

Analysis of Anxiety of BEC1-overexpressing Transgenic Mouse by Light and Shade In order to analyze the action of BEC1 overexpression upon animals, a light/dark exploration test was carried out using # 9-5 line transgenic mice and wild type mice. The light/dark explorationing boxes (mfd. by Muromachi Kikai) comprise a 30 cm square light box and an adjoining dark box of 30 cm×20 cm, and a mouse can freely passes these two boxed through a small hole. Each mouse was put into the exploration boxes for 5 minutes, and the time spent in each box and the number of transitions between the light and dark box were counted by an infrared sensor. As a result, the number of transitions (average value±standard deviation) of the wild type was 14.3±1.5, while it was significantly reduced to 9.4±1.9 in the transgenic mice ($p<0.05$, Student's t test). Also, the light box staying time was 61.4±4.9 seconds in the wild type, but was 42.4±7.5 seconds in the transgenic mice showing significant reduction ($p<0.05$, Student's t test). It was shown that anxiety is accelerated in the transgenic mice. By this method which uses BEC1 transgenic mice, a substance for antianxiety can be screened.

Example 7

Analysis of LTP in Hippocampus CA1 of BEC1-overexpressing Transgenic Mouse

It is considered that LTP, a phenomenon in which synaptic transmission efficiency is increased over a long period of time, is a basic process of learning and memory. In order to analyze the action of BEC1 overexpression upon LTP, comparison of LTP in the hippocampus CA1 of # 9-5 line transgenic mice and wild type mice was carried out.

Hippocampus slices were prepared from 5 animals of each of the transgenic mouse and wild type mouse of 3 months of age after birth. Preparation of the hippocampus slices was carried out in accordance with the method of Edwards, F A et al. (1989), "A thin slice preparation for patch clamp recordings from neurons of the mammalian central nervous system", *Pflegers Arch.*, 414, 600–612. The extracellular electric field potential was recorded using Multi-Electrode Dish (mfd. by Matsushita Electric Industrial, Oka H et al., (1999), J. Neurosci. Methods, 93, 61–67) on which each slice was arranged. The synaptic response of CA1 pyramidal cell was induced by stimulating the Shuffer collateral/comissural fibers —CA1 pathway. In the slice of wild type mouse, tetanus stimulation (100 Hz, 1 second) induced increase of the synaptic reaction (243±26.9% 45 minutes after the tetanus stimulation). On the other hand, similar stimulation induced only a significantly small increase (126±13.6%, $p<0.05$ by Student's t test) in the slice of transgenic mouse. It was shown that the hippocampus LTP is inhibited in the transgenic mouse.

These results suggest a possibility that BEC1 is causing the impairment in learning and memory by inhibiting formation of the hippocampus LTP. The hippocampus LTP of this transgenic mouse is useful as an index of a substance for antidementia or a substance to improve learning and memory.

Example 8

In Vivo Screening of a Substance for Antidementia or a Substance to Improve Learning and Memory Using Learning and Memory Potassium Channel Inhibitory Action as the Mechanism In vivo screening of a substance for antidementia or a substance to improve learning and memory using learning and memory potassium channel inhibitory action as the mechanism was carried out by a passive avoidance test similar to Example 5. Each of the compounds to be tested was suspended in 0.5% methyl cellulose physiological saline and intraperitoneally administered 30 minutes before or just after the constant voltage stimulation. The mouse was again put into the light box 24 hours thereafter, and the shaded box-entering time at this time was measured. One compound having the effect to prolong the shaded box-entering time in comparison with the 0.5% methyl cellulose physiological saline-administered group was obtained. It can be judged that this compound has an anti-dementia effect or a learning and memory improving effect.

INDUSTRIAL APPLICABILITY

By the screening method of the present invention, a substance useful as a substance for antidementia, a substance to improve learning and memory or a substance for antianxiety can be in vivo screened.

In vivo screening of a substance for antidementia or a substance to improve learning and memory, which uses the learning and memory potassium channel inhibitory action as the mechanism, can be carried out by using the learning and memory abilities of the transgenic animal of the present invention as the index, and in vivo screening of a substance for antianxiety, which uses the learning and memory potassium channel inhibitory action as the mechanism, can be carried out by using anxiety of the same animal as the index. That is, the transgenic animal of the present invention can be used as a tool for screening a substance for antidementia, a substance to improve learning and memory or a substance for antianxiety.

In addition, a pharmaceutical composition for antidementia, learning and memory improvement use or antianxiety can be produced, using a substance capable of inhibiting the learning and memory potassium channel activity, which can be obtained by the screening method of the present invention, as the active ingredient, and making it into a pharmaceutical preparation using a carrier, a filler and/or other additive agents.

Sequence Listing Free Text

Description on the "Artificial Sequence" is described in the numeral index <223> of the following Sequence Listing. Illustratively, respective nucleotide sequences represented by SEQ ID NOs:3, 6, 7 and 8 in the Sequence Listing are artificially synthesized primer sequences.

Though the present invention has been described in the foregoing based on specific embodiments, modifications and improvements obvious to those skilled in the art are included in the scope of the invention.

The invention claimed is:

1. A transgenic mouse whose genome comprises a transgene comprising a polynucleotide encoding a potassium channel polypeptide wherein said potassium channel polypeptide comprises the sequence set forth in SEQ ID NO: 2, wherein said polynucleotide is operably linked to a neuronal cell specific promoter, wherein said potassium channel polypeptide is expressed in the brain of said transgenic mouse, and wherein said transgenic mouse exhibits reduced learning and memory abilities, dementia, or anxiety.

2. The transgenic mouse of claim 1, wherein said promoter is an α-calcium-calmodulin-dependent kinase II promoter.

3. A method for detecting a substance that inhibits a potassium channel, said method comprising administering a candidate substance to the transgenic mouse of claim 1, measuring anxiety in said transgenic mouse and comparing a change in anxiety to a control mouse.

4. A method for detecting a substance that inhibits anxiety, said method comprising administering a candidate substance to the transgenic mouse of claim 1, measuring anxiety in said transgenic mouse and comparing a change in anxiety to a control mouse.

5. A method for screening a substance for anti-anxiety activity, said method comprising administering a candidate substance to the transgenic mouse of claim 1, measuring anxiety in said transgenic mouse, and selecting a substance having an anxiety inhibiting effect.

* * * * *